United States Patent [19]
Wilde

[11] Patent Number: 6,075,001
[45] Date of Patent: Jun. 13, 2000

[54] ENOL ESTERS AS BLEACH ACTIVATORS FOR DETERGENTS AND CLEANERS

[75] Inventor: Andreas Wilde, Duesseldorf, Germany

[73] Assignee: Henkel Kommanditgesellschaft aug Aktien, Duesseldorf, Germany

[21] Appl. No.: 09/171,791

[22] PCT Filed: Apr. 17, 1997

[86] PCT No.: PCT/EP97/01930

§ 371 Date: Oct. 26, 1998

§ 102(e) Date: Oct. 26, 1998

[87] PCT Pub. No.: WO97/41201

PCT Pub. Date: Nov. 6, 1997

[30] Foreign Application Priority Data

Apr. 26, 1996 [DE] Germany ............ 196 16 693

[51] Int. Cl.[7] ............ C11D 3/39; C11D 3/395; C11D 7/18; C11D 7/54; A61K 33/40
[52] U.S. Cl. ............ 510/376; 510/312; 510/378
[58] Field of Search ............ 510/376, 378, 510/382, 302, 309, 312

[56] References Cited

U.S. PATENT DOCUMENTS

| | | | |
|---|---|---|---|
| 4,585,642 | 4/1986 | Rieck | 423/333 |
| 4,664,839 | 5/1987 | Rieck | 252/175 |
| 4,820,439 | 4/1989 | Rieck | 252/135 |
| 4,985,553 | 1/1991 | Fuertes et al. | 536/124 |
| 5,183,651 | 2/1993 | Schimmel et al. | 423/334 |
| 5,229,095 | 7/1993 | Schimmel et al. | 423/334 |
| 5,236,682 | 8/1993 | Schimmel et al. | 423/334 |
| 5,268,156 | 12/1993 | Schimmel et al. | 423/334 |
| 5,308,596 | 5/1994 | Kotzian et al. | 423/333 |
| 5,318,733 | 6/1994 | Carduck et al. | 264/15 |
| 5,356,607 | 10/1994 | Just | 423/334 |
| 5,358,655 | 10/1994 | Kruse et al. | 252/95 |
| 5,417,951 | 5/1995 | Just | 423/334 |
| 5,494,488 | 2/1996 | Arnoldi et al. | 8/137 |
| 5,541,316 | 7/1996 | Engelskirchen et al. | 510/471 |
| 5,580,941 | 12/1996 | Krause et al. | 527/300 |

FOREIGN PATENT DOCUMENTS

| | | |
|---|---|---|
| 1 036 455 | 8/1978 | Canada . |
| 0 092 932 | 11/1983 | European Pat. Off. . |
| 0 122 763 | 10/1984 | European Pat. Off. . |
| 0 164 514 | 12/1985 | European Pat. Off. . |
| 0 164 552 | 12/1985 | European Pat. Off. . |
| 0 232 202 | 8/1987 | European Pat. Off. . |
| 0 294 753 | 12/1988 | European Pat. Off. . |
| 0 425 427 | 5/1991 | European Pat. Off. . |
| 0 425 428 | 5/1991 | European Pat. Off. . |
| 0 436 835 | 7/1991 | European Pat. Off. . |
| 0 502 325 | 9/1992 | European Pat. Off. . |
| 0 548 599 | 6/1993 | European Pat. Off. . |
| 0 564 476 | 10/1993 | European Pat. Off. . |
| 0 579 659 | 1/1994 | European Pat. Off. . |
| 0 591 282 | 4/1994 | European Pat. Off. . |
| 0 486 592 | 6/1994 | European Pat. Off. . |
| 0 733 701 | 9/1996 | European Pat. Off. . |
| 24 12 837 | 10/1974 | Germany . |
| 30 03 351 | 8/1981 | Germany . |
| 42 21 381 | 2/1994 | Germany . |
| 43 00 772 | 7/1994 | Germany . |
| 43 03 320 | 8/1994 | Germany . |
| 44 17 734 | 11/1995 | Germany . |
| 04 238 809 | 8/1992 | Japan . |
| 04 260 610 | 9/1992 | Japan . |
| 2 294 045 | 4/1996 | United Kingdom . |
| WO91/08171 | 6/1991 | WIPO . |
| WO92/18542 | 10/1992 | WIPO . |
| WO93/16110 | 8/1993 | WIPO . |
| WO94/23005 | 10/1994 | WIPO . |
| WO95/22592 | 8/1995 | WIPO . |

OTHER PUBLICATIONS

Schmidt, et al., Synthesis, Georg Thieme Verlag, Stuttgart, New York (1982) pp. 958–962.

Chigira, et al., "Syntheses and Reactions of N–(Phenylpyruvoyl) Amino Acids", Bull. Chem. Soc. Jpn., vol. 42 (1969) pp. 224–228.

Primary Examiner—Yogendra Gupta
Assistant Examiner—John M Petruncio
Attorney, Agent, or Firm—Wayne C. Jaeschke; Steven J. Trzaska; Glen E. J. Murphy

[57] ABSTRACT

A composition containing: (a) a peroxygen compound; and (b) an activator compound corresponding to formula I:

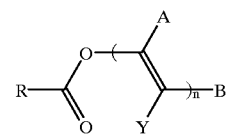

(I)

wherein R is hydrogen, an aryl, alkyl, alkenyl or cycloalkyl group containing 1 to 17 carbon atoms, n is a number from 1 to 8, A, B and Y, independently of one another, represent hydrogen, an aryl, alkyl, alkenyl or cycloalkyl group containing 1 to 17 carbon atoms or a hydrophilic group selected from the group consisting of $-SO_3H$, $-OSO_3H$, $-PO(OH)_2$, $-OPO(OH)_2$, $-CO_2H$ and anions thereof and $-N^+R^1R^2R^3X^-$, where $R^1$, $R^2$ and $R^3$, independently of one another, represent hydrogen, an aryl, alkyl, alkenyl or cycloalkyl group containing 1 to 17 carbon atoms and $X^-$ represents a charge-equalizing anion, and wherein at least one of the substituents A, B or Y in the molecule is one of the hydrophilic groups.

20 Claims, No Drawings

ENOL ESTERS AS BLEACH ACTIVATORS FOR DETERGENTS AND CLEANERS

BACKGROUND OF THE INVENTION

1. Field of the Invention

This invention relates to the use of hydrophilically substituted enol esters as bleach activators for activating peroxygen compounds, more particularly for bleaching colored stains in the washing of textiles, and to detergents, cleaners and disinfectants containing such bleach activators.

2. Discussion of Related Art

Inorganic peroxygen compounds, more particularly hydrogen peroxide, and solid peroxygen compounds which dissolve in water with elimination of hydrogen peroxide, such as sodium perborate and sodium carbonate perhydrate, have long been used as oxidizing agents for disinfecting and bleaching purposes. In dilute solutions, the oxidizing effect of these substances depends to a large extent on the temperature. For example, with $H_2O_2$ or perborate in alkaline bleaching liquors, sufficiently rapid bleaching of soiled textiles is only achieved at temperatures above about 80° C. At lower temperatures, the oxidizing effect of the inorganic peroxygen compounds can be improved by addition of so-called bleach activators which are capable of forming peroxocarboxylic acids under the described perhydrolysis conditions and for which numerous proposals, above all from the classes of N- or O-acyl compounds, for example polyacylated alkylenediamines, more particularly tetraacetyl ethylenediamine, acylated glycolurils, more particularly tetraacetyl glycoluril, N-acylated hydantoins, hydrazides, triazoles, hydrotriazines, urazoles, diketopiperazines, sulfuryl amides and cyanurates, also carboxylic anhydrides, more particularly phthalic anhydride, carboxylic acid esters, more particularly sodium nonanoyloxybenzenesulfonate, sodium isononanoyloxybenzenesulfonate, O-acylated sugar derivatives, such as pentaacetyl glucose, and N-acylated lactams, such as N-benzoyl caprolactam, can be found in the literature. By adding these substances, the bleaching effect of aqueous peroxide liquors can be increased to such an extent that substantially the same effects are obtained at temperatures of only 60° C. as are obtained with the peroxide liquor alone at 95° C.

In the search for energy-saving washing and bleaching processes, operating temperatures well below 60° C. and, more particularly, below 45° C. down to the temperature of cold water have acquired increasing significance in recent years.

At these low temperatures, there is generally a discernible reduction in the effect of known activator compounds. Accordingly, there has been no shortage of attempts to develop more effective activators for this temperature range although the results achieved thus far have not been convincing.

The use of enol esters optionally bearing $C_{1-5}$ alkyl or $C_{2-4}$ alkenyl groups at the enolic double bond as bleach activators is recommended in European patent applications EP 0 092 932 A1 and EP 0 122 763 A2. It has now surprisingly been found that enol esters bearing at least one hydrophilic group have a distinctly stronger bleach-activating effect.

DESCRIPTION OF THE INVENTION

Accordingly, the present invention relates to the use of compounds corresponding to general formula I:

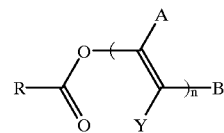

in which R represents hydrogen, an aryl, alkyl, alkenyl or cycloalkyl group containing 1 to 17 carbon atoms, n is a number of 1 to 8, A, B and Y independently of one another represent hydrogen, an aryl, alkyl, alkenyl or cycloalkyl group containing 1 to 17 carbon atoms or a hydrophilic group selected from $-SO_3H$, $-OSO_3H$, $-PO(OH)_2$, $-OPO(OH)_2$, $-CO_2H$ and anions thereof and $-N^+R^1R^2R^3$ $X^-$, where $R^1$, $R^2$ and $R^3$ independently of one another represent hydrogen, an aryl, alky, alkenyl or cycloalkyl group containing 1 to 17 carbon atoms and $X^-$ represents a charge-equalizing anion, with the proviso that at least one of the substituents A, B or Y in the molecule is one of the hydrophilic groups mentioned, as activators for peroxygen compounds, more particularly inorganic peroxygen compounds, in oxidizing, washing, cleaning or disinfecting solutions.

Preferred compounds corresponding to formula (I) are those in which R represents phenyl, $C_{1-11}$ alkyl, 9-decenyl and mixtures thereof, the alkyl groups being linear or branched. Among the compounds corresponding to formula (I) with linear alkyl groups R, those containing 1 to 9 carbon atoms in the alkyl chain R are particularly preferred.

A preferred embodiment of the invention is characterized by the use of mixtures of compounds I yielding different peroxocarboxylic acids, more particularly those yielding optionally substituted perbenzoic acid and/or peroxocarboxylic acids containing 1 to 5 and, more particularly, 2 to 4 carbon atoms under perhydrolysis conditions, with those yielding linear or branched-chain peroxocarboxylic acids containing 6 to 18 and, more particularly, 7 to 12 carbon atoms under perhyrolysis conditions. For use in particulate detergents, cleaners and disinfectants, the compounds of formula I to be used in accordance with the invention are preferably solid at room temperature.

The hydrophilic groups, of which at least one is present in the enol esters to be used in accordance with the invention, are selected from the sulfonate, sulfate, phosphonate, phosphate and carboxylate groups, which may also be present in protonated form, and the ammonium groups. If the anionic groups mentioned are present, counter-cations, preferably alkali metal ions, such as sodium, potassium and/or lithium ions, are present. If an ammonium group is present, charge-equalizing anions $X^-$, preferably halides, such as chloride, bromide, iodide and/or fluoride, are present.

Preferred representatives of the compounds corresponding to general formula I include the enol esters derived from the enol form of glutaconic acid monoaldehyde which correspond to general formula II:

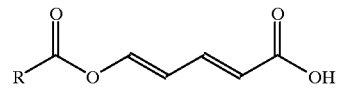

and the enol esters derived from the enol form of phenylpyruvic acid which correspond to general formula III:

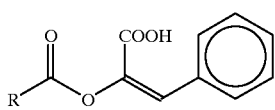

(III)

where R is as defined above and of which the carboxyl group may also be present in salt form.

The compounds to be used in accordance with the invention may be obtained by the methods known from the Articles by R. Schmidt and A. Wagner in *Synthesis* 1982, pages 958 et seq and Y. Chigata, M. Masaki and M. Ohta in *Bull. Chem. Soc. Jpn.* 42 (1969), pages 224 et seq or similar methods.

The compounds corresponding to formula I are preferably used for bleaching colored stains in the washing of textiles, particularly in a water-based surfactant-containing liquor. The expression "bleaching of colored stains" is meant to be interpreted in its broadest sense and encompasses both the bleaching of soil present on the textiles, the bleaching of soil detached from the textiles and present in the wash liquor and the oxidative destruction of textile dyes present in the wash liquor—which are detached from textiles under the washing conditions—before they can be absorbed by differently colored textiles.

In another preferred embodiment, the present invention relates to the use of compounds corresponding to formula I in cleaning solutions for hard surfaces, more particularly for crockery, for bleaching colored stains. In this case, too, the term "bleaching" applies both to the bleaching of soil, particularly tea, present on the hard surface and to the bleaching of soil suspended in the dishwashing liquor after detachment from the hard surface.

The present invention also relates to detergents, cleaners and disinfectants containing a compound corresponding to formula I as bleach activator and to a process for activating peroxygen compounds using a compound corresponding to formula I.

In the process according to the invention and in the use according to the invention, the compounds corresponding to formula I may be used as activators anywhere where a particular increase in the oxidizing effect of inorganic peroxygen compounds at low temperatures is required, for example in the bleaching of textiles, hair or hard surfaces, in the oxidation of organic or inorganic intermediates and in disinfection.

The use according to the invention essentially comprises creating conditions under which a peroxygen compound and a compound corresponding to formula I can react with one another with a view to obtaining products with a stronger oxidizing effect. Such conditions prevail in particular when both reactants meet in an aqueous solution. This can be achieved by separately adding the peroxygen compound and the bleach activator to a solution optionally containing a detergent or cleaner. In one particularly advantageous embodiment, however, the process according to the invention is carried out using a detergent, cleaner or disinfectant according to the invention which contains the bleach activator corresponding to formula I and optionally a peroxidic oxidizing agent. The peroxygen compound may even be separately added to the washing, cleaning or disinfecting solution as such or preferably in the form of an aqueous solution or suspension in cases where a peroxygen-free formulation is used.

The conditions can be widely varied according to the application envisaged. Thus, besides purely aqueous solutions, mixtures of water and suitable organic solvents may serve as the reaction medium. The quantities of peroxygen compounds used are generally selected so that the solutions contain between 10 ppm and 10% of available oxygen and preferably between 50 and 5000 ppm of available oxygen. The quantity of bleach activator corresponding to formula I used is also determined by the particular application envisaged. Depending on the required degree of activation, the bleach activator corresponding to formula I to be used in accordance with the invention is used in such a quantity that 0.03 mole to 1 mole and preferably 0.1 mole to 0.5 mole of bleach activator is used per mole of peroxygen compound, although quantities above and below these limits may be used in special cases.

A detergent, cleaner or disinfectant according to the invention preferably contains 0.2% by weight to 30% by weight and, more particularly, 1% by weight to 20% by weight of bleach activator corresponding to formula I in addition to typical ingredients compatible with the bleach activator. The activating substances to be used in accordance with the invention may be adsorbed onto supports and/or encapsulated in shell-forming substances by methods known in principle.

In addition to the bleach activator corresponding to formula I to be used in accordance with the invention, the detergents, cleaners and disinfectants according to the invention, which may be present in the form of —in particular—powder-form solids, in the form of post-compacted particles or in the form of homogeneous solutions or suspensions, may in principle contain any known ingredients typically encountered in such formulations. In particular, the detergents and cleaners according to the invention may contain builders, surfactants, organic and/or in particular inorganic peroxygen compounds, water-miscible organic solvents, enzymes, sequestering agents, electrolytes, pH regulators and other auxiliaries, such as optical brighteners, redeposition inhibitors, dye transfer inhibitors, foam regulators, additional peroxygen activators, dyes and perfumes.

In addition to the ingredients mentioned thus far, a disinfectant according to the invention may contain typical antimicrobial agents to enhance its disinfecting effect on special germs. Antimicrobial additives of the type in question are present in the disinfectants according to the invention in quantities of preferably up to 10% by weight and, more preferably, in quantities of 0.1% by weight to 5% by weight.

Typical compounds which form peroxocarboxylic acids under perhydrolysis conditions, as mentioned at the beginning, and/or typical bleach-activating transition metal complexes may be used in addition to the bleaching activators corresponding to formula I to be used in accordance with the invention.

Suitable peroxygen compounds are, in particular, organic peracids or peracidic salts of organic acids, such as phthalimidopercaproic acid, perbenzoic acid or salts of diperdodecanedioic acid, hydrogen peroxide and inorganic salts which give off hydrogen peroxide under the washing or cleaning conditions, such as perborate, percarbonate and/or persilicate. If solid peroxygen compounds are to be used, they may be employed in the form of powders or granules which may even be coated by methods known in principle. The peroxygen compounds may be added to the wash or cleaning liquor as such or in the form of preparations containing them in which, basically, any typical ingredients of detergents, cleaners or disinfectants may be present. In one particularly preferred embodiment, alkali metal percarbonanate, alkali metal perborate monohydrate or hydrogen peroxide is used in the form of an aqueous solution containing 3% by weight to 10% by weight of hydrogen peroxide. If a detergent or cleaner according to the invention contains peroxygen compounds, the peroxygen compounds are present in quantities of preferably up to 50% by weight and more particularly from 5% by weight to 30% by weight whereas the disinfectants according to the invention contain preferably from 0.5% by weight to 40% by weight and more preferably from 5% by weight to 20% by weight of peroxygen compounds.

The formulations according to the invention may contain one or more surfactants, more particularly anionic surfactants, nonionic surfactants and mixtures thereof. Suitable nonionic surfactants are, in particular, alkyl glycosides and ethoxylation and/or propoxylation products of alkyl glycosides or linear or branched alcohols containing 12 to 18 carbon atoms in the alkyl group and 3 to 20 and preferably 4 to 10 alkyl ether groups. Corresponding ethoxylation and/or propoxylation products of N-alkylamines, vicinal diols, fatty acid esters and fatty acid amides corresponding to the long-chain alcohol derivatives mentioned in regard to the alkyl moiety and of alkyl-phenols containing 5 to 12 carbon atoms in the alkyl group may also be used.

Suitable anionic surfactants are, in particular, soaps and those which contain sulfate or sulfonate groups preferably having alkali metal ions as cations. Preferred soaps are the alkali metal salts of saturated or unsaturated fatty acids containing 12 to 18 carbon atoms. Fatty acids such as these need not even be completely neutralized for use in accordance with the invention. Suitable surfactants of the sulfate type include salts of sulfuric acid semi-esters of fatty alcohols containing 12 to 18 carbon atoms and sulfation products of the nonionic surfactants mentioned with a low degree of ethoxylation. Suitable surfactants of the sulfonate type include linear alkylbenzenesulfonates containing 9 to 14 carbon atoms in the alkyl moiety, alkanesulfonates containing 12 to 18 carbon atoms and olefin sulfonates containing 12 to 18 carbon atoms, which are formed in the reaction of corresponding monoolefins with sulfur trioxide, and also α-sulfofatty acid esters which are formed in the sulfonation of fatty acid methyl or ethyl esters.

Surfactants such as these are present in the cleaners or detergents according to the invention in quantities of, preferably, 5% by weight to 50% by weight and, more preferably, 8% by weight to 30% by weight while the disinfectants according to the invention and machine dishwashing detergents according to the invention preferably contain 0.1 % by weight to 20% by weight and, more preferably, 0.2% by weight to 5% by weight of surfactants.

A formulation according to the invention preferably contains at least one water-soluble and/or water-insoluble, organic and/or inorganic builder. Water-soluble organic builders include polycarboxylic acids, more particularly citric acid and sugar acids, monomeric and polymeric aminopolycarboxylic acids, more particularly methyl glycine diacetic acid, nitrilotriacetic acid and ethylenediamine tetraacetic acid, and polyaspartic acid, polyphosphonic acids, more particularly aminotris-(methylenephosphonic acid), ethylene-diamine tetrakis(methylenephosphonic acid) and 1-hydroxyethane-1,1-diphosphonic acid, polymeric hydroxy compounds, such as dextrin, and polymeric (poly)carboxylic acids, more particularly the polycarboxylates obtainable by oxidation of polysaccharides or dextrins according to International patent application WO 93/16110, International patent application WO 92/18542 or European patent EP 0 232 202, polymeric acrylic acids, methacrylic acids, maleic acids and copolymers thereof which may also contain small amounts of polymerizable substances with no carboxylic acid functionality in copolymerized form. The relative molecular weight of the homopolymers of unsaturated carboxylic acids is generally in the range from 5,000 to 200,000 while the relative molecular weight of the copolymers is between 2,000 and 200,000 and preferably between 50,000 and 120,000, based on free acid. A particularly preferred acrylic acid/maleic acid copolymer has a relative molecular weight of 50,000 to 100,000. Suitable, albeit less preferred, compounds of this class are copolymers of acrylic acid or methacrylic acid with vinyl ethers, such as vinyl methyl ethers, vinyl esters, ethylene, propylene and styrene, in which the acid makes up at least 50% by weight of the copolymer. Other suitable water-soluble organic builders are terpolymers which contain two unsaturated acids and/or salts thereof as monomers and vinyl alcohol and/or an esterified vinyl alcohol or a carbohydrate as the third monomer. The first acidic monomer or its salt is derived from a monoethylenically unsaturated $C_{3-8}$ carboxylic acid and preferably from a $C_{3-4}$ monocarboxylic acid, more particularly from (meth)acrylic acid. The second acidic monomer or its salt may be a derivative of a $C_{4-8}$ dicarboxylic acid, maleic acid being particularly preferred, and/or a derivative of an allylsulfonic acid substituted in the 2-position by an alkyl or aryl group. Polymers such as these may be produced in particular by the processes described in German patent DE 42 21 381 and in German patent application DE 43 00 772 and generally have a relative molecular weight in the range from 1,000 to 200,000. Other preferred copolymers are the copolymers which are described in German patent applications DE 43 03 320 and DE 44 17 734 and which preferably contain acrolein and acrylic acid/acrylic acid salts or vinyl acetate as monomers. The organic builders may be used in the form of aqueous solutions, preferably 30 to 50% by weight aqueous solutions, particularly for the production of liquid formulations. All the acids mentioned are generally used in the form of their water-soluble salts, more particularly their alkali metal salts.

If desired, organic builders of the type in question may be present in quantities of up to 40% by weight, more particularly in quantities of up to 25% by weight and preferably in quantities of 1% by weight to 8% by weight Quantities near the upper limit mentioned are preferably used in paste-form or liquid, more particularly water-containing, formulations according to the invention.

Particularly suitable water-soluble inorganic builders are polyphosphates, preferably sodium tripolyphosphate. Particularly suitable water-insoluble, water-dispersible inorganic builders are crystalline or amorphous alkali metal alumosilicates used in quantities of up to 50% by weight and preferably in quantities of not more than 40% by weight and, in liquid formulations, particularly in quantities of 1% by weight to 5% by weight. Of these inorganic builders, detergent-range crystalline sodium alumosilicates, more particularly zeolite A, P and optionally X, are preferred. Quantities approaching the upper limit mentioned are preferably used in solid particulate formulations. Suitable alumosilicates contain in particular no particles larger than 30 $\mu$m in size, at least 80% by weight preferably consisting of particles below 10 $\mu$m in size. Their calcium binding capacity, which may be determined in accordance with German patent DE 24 12 837, is generally in the range from 100 to 200 mg CaO per gram.

Suitable substitutes or partial substitutes for the alumosilicate mentioned are crystalline alkali metal silicates which may be present either on their own or in the form of a mixture with amorphous silicates. The alkali metal silicates suitable for use as builders in the formulations according to the invention preferably have a molar ratio of alkali metal oxide to $SiO_2$ of less than 0.95:1 and, more particularly, from 1:1.1 to 1:12 and may be present in amorphous or crystalline form. Preferred alkali metal silicates are the sodium silicates, more particularly the amorphous sodium silicates, with a molar $Na_2O:SiO_2$ ratio of 1:2 to 1:2.8. Those with a molar $Na_2O:SiO_2$ ratio of 1:1.9 to 1:2.8 may be produced by the process according to European patent application EP 0 425 427. Preferred crystalline silicates, which may be present either on their own or in the form of a mixture with amorphous silicates, are crystalline layer silicates with the general formula $Na_2Si_xO_{2x+1}yH_2O$, where x—the so-called modulus—is a number of 1.9 to 4 and y is a number of 0 to 20, preferred values for x being 2, 3 or 4. Crystalline layer silicates which correspond to this general formula are described, for example, in European patent application EP 0 164 514. Preferred crystalline layer silicates are those in which x in the general formula mentioned assumes a value of 2 or 3. Both β- and ō-sodium disilicates $(Na_2Si_2O_5yH_2O)$ are particularly preferred, β-sodium disilicate being obtainable, for example, by the process described in International patent application WO 91/08171. ō-Sodium silicates with a modulus of 1.9 to 3.2 may be produced in accordance with Japanese patent applications JP 04/238 809 or JP 04/260 610. Substantially water-free crystalline alkali metal silicates corresponding to the above general formula, in which x is a number of 1.9 to 2.1, obtainable from amorphous alkali metal silicates as described in European patent applications EP 0 548 599, EP 0 502 325 and EP 0 25 428, may also be used in the formulations according to the invention. Another preferred embodiment of formulations according to the invention uses a crystalline sodium layer silicate with a modulus of 2 to 3 obtainable from sand and soda by the process according to European patent application EP 0 436 835. Crystalline sodium silicates with a modulus of 1.9 to 3.5 obtainable by the processes according to European patents EP 0 164 552 and/or EP 0 294 753 are used in another preferred embodiment of the formulations according to the invention. Another preferred embodiment of the formulations according to the invention is characterized by the use of the granular compound of alkali metal silicate and alkali metal carbonate which is described for example in International patent application WO 95/22592 or which is commercially obtainable, for example, under the name Nabion®15. If alkali metal alumosilicate, particularly zeolite, is present as an additional builder, the ratio by weight of alumosilicate to silicate, expressed as water-free active substances, is preferably from 1:10 to 10:1. In formulations containing both amorphous and crystalline alkali metal silicates, the ratio by weight of amorphous alkali metal silicate to crystalline alkali metal silicate is preferably 1:2 to 2:1 and, more preferably, 1:1 to 2:1.

Builders are present in the detergents or cleaners according to the invention in quantities of, preferably, up to 60% by weight and, more preferably, from 5% by weight to 40% by weight while the disinfectants according to the invention are preferably free from the builders which only complex the components of water hardness and contain preferably no more than 20% by weight and, more preferably, from 0.1% by weight to 5% by weight of heavy metal complexing agents, preferably from the group consisting of aminopolycarboxylic acids, aminopolyphosphonic acids and hydroxypolyphosphonic acids and water-soluble salts and mixtures thereof.

Enzymes suitable for use in the detergents/cleaners/disinfectants are enzymes from the class of proteases, lipases, cutinases, amylases, pullulanases, cellulases, hemicellulases, xylanases, oxidases and peroxidases and mixtures thereof. Particularly suitable enzymes are those obtained from fungi or bacteria, such as *Bacillus subtilis, Bacillus licheniformis, Streptomyces griseus, Humicola lanuginosa, Humicola insolens, Pseudomonas pseudoalcaligenes* or *Pseudomonas cepacia*. As described for example in European patent EP 0 564 476 or in International patent application WO 94/23005, the enzymes optionally used may be adsorbed onto supports and/or encapsulated in shell-forming substances to protect them against premature inactivation. They are added to the detergents, cleaners and disinfectants according to the invention in quantities of preferably up to 5% by weight and, more preferably, between 0.2% by weight and 2% by weight.

Organic solvents suitable for use in the formulations according to the invention, particularly where they are present in liquid or paste-like form, include alcohols containing 1 to 4 carbon atoms, more particularly methanol, ethanol, isopropanol and tert.butanol, diols containing 2 to 4 carbon atoms, more particularly ethylene glycol and propylene glycol, and mixtures thereof and the ethers derived from compounds belonging to the classes mentioned above. Water-miscible solvents such as these are present in the detergents, cleaners and disinfectants according to the invention in quantities of preferably not more than 30% by weight and, more preferably, in quantities of 6% by weight to 20% by weight.

To establish a desired pH value which is not automatically adjusted by the mixture of the other components, the formulations according to the invention may contain system-compatible and ecologically compatible acids, more particularly citric acid, acetic acid, tartaric acid, malic acid, lactic acid, glycolic acid, succinic acid, glutaric acid and/or adipic acid, and mineral acids, more particularly sulfuric acid, or bases, more particularly ammonium or alkali metal hydroxides. pH regulators such as these are present in the formulations according to the invention in quantities of preferably not more than 20% by weight and, more preferably, between 1.2% by weight and 17% by weight.

Dye transfer inhibitors suitable for use in formulations according to the invention, especially laundry detergents, include in particular polyvinyl pyrrolidones, polyvinyl imidazoles, polymeric N-oxides, such as poly-(vinylpyridine-N-oxide) and copolymers of vinyl pyrrolidone with vinyl imidazole.

The function of redeposition inhibitors is to keep the soil detached from the hard surface and especially from the textile fibers suspended in the wash liquor. Suitable redeposition inhibitors are water-soluble, generally organic colloids, for example starch, glue, gelatine, salts of ether carboxylic acids or ether sulfonic acids of starch or cellulose or salts of acidic sulfuric acid esters of cellulose or starch. Water-soluble polyamides containing acidic groups are also suitable for this purpose. Other starch derivatives than those mentioned above, for example aldehyde starches, may also be used. However, cellulose ethers, such as carboxymethyl cellulose (Na salt), methyl cellulose, hydroxyalkyl cellulose, and mixed ethers, such as methyl hydroxyethyl cellulose, methyl hydroxypropyl cellulose, methyl carboxymethyl cellulose and mixtures thereof, may also be used, for example in quantities of 0.1 to 5% by weight, based on the formulation.

The formulations may contain derivatives of diaminostilbene disulfonic acid or alkali metal salts thereof as optical brighteners. Suitable optical brighteners are, for example, salts, of 4,4'-bis-(2-anilino-4-morpholino-1,3,5-triazinyl-6amino)-stilbene-2,2'-disulfonic acid or compounds of similar composition which contain a diethanolamino group, a methylamino group, an anilino group or a 2-methoxyethylamino group instead of the morpholino group. Brighteners of the substituted diphenyl styryl type, for example alkali metal salts of 4,4'-bis-(2-sulfostyryl)-diphenyl, 4,4'-bis-(4-chloro-3-sulfostyryl)-diphenyl or 4-(4-chlorostyryl)4'-(2-sulfostyryl)-diphenyl, may also be present. Mixtures of the brighteners mentioned above may also be used.

Where the formulations are used in machine washing and cleaning processes, it can be of advantage to add typical foam inhibitors to them. Suitable foam inhibitors are, for example, soaps of natural or synthetic origin with a high percentage content of $C_{18-24}$ fatty acids. Suitable non-surface-active foam inhibitors are, for example, organopolysiloxanes and mixtures thereof with microfine, optionally silanized silica and also paraffins, waxes, microcrystalline waxes and mixtures thereof with silanized silica or bis-fatty acid alkylene diamides. Mixtures of various foam inhibitors, for example mixtures of silicones, paraffins or waxes, are also used with advantage. The foam inhibitors, more particularly silicone- and/or paraffin-containing foam inhibitors, are preferably fixed to a granular water-soluble or water-dispersible support. Mixtures of paraffins and bis-stearyl ethylenediamides are particularly preferred.

Dishwashing detergents according to the invention may additionally contain chemicals to prevent silverware from tarnishing, so-called silver corrosion inhibitors. Preferred silver corrosion inhibitors are organic disulfides, dihydric phenols, trihydric phenols, optionally alkyl- or aminoalkyl-substituted triazoles, such as benzotriazole, and cobalt, manganese, titanium, zirconium, hafnium, vanadium or cerium salts and/or complexes in which the metals mentioned are present with one of the oxidation numbers II, III, IV, V or VI.

The production of solid formulations according to the invention does not involve any difficulties and may be carried out by methods known in principle, for example by spray drying or granulation, the peroxygen compound and bleach activator optionally being added later. To produce formulations according to the invention with high bulk density, more particularly in the range from 650 g/l to 950 g/l, a process comprising an extrusion step known from European patent EP 486 592 is preferably applied. Detergents, cleaners or disinfectants according to the invention in the form of aqueous solutions or solutions containing other typical solvents are produced with particular advantage simply by mixing the ingredients which may be introduced into an automatic mixer either as such or in the form of a solution. In one preferred embodiment of machine dishwashing formulations, the formulations are produced in the form of tablets by the processes disclosed in European patents EP 0 579 659 and EP 0 591 282.

EXAMPLES

Phenylpyruvic acid acetate according to the invention (B1; see general formula III, R=$CH_3$) prepared from phenylpyruvic acid and acetic anhydride by R. Schmidt and A. Wagner's method, as described in *Synthesis* 982 pages 958 et seq, and for comparison N,N,N',N'-tetraacetyl ethylenediamine (C1; TAED), sodium-n-nonanoyloxybenzenesulfonate (C2; n-NOBS) and the enol ester isopropenyl nonanoate which does not correspond to the invention (C3) were tested for their bleaching effect at 30° C./pH 10. To this end, 2 ml of red wine, 138 mg of sodium perborate monohydrate and the quantity of activator shown in the following Table (=active oxygen, based on the peroxocarboxylic acid formed) were added to 100 ml of a wash liquor containing in 5 l (rest distilled water) 2.5 g of sodium alkylene benzene-sulfonate, 2 g of fatty alkyl ethoxylate, 10 g of sodium tripolyphosphate, 1.5 g of sodium silicate, 7.5 g of sodium sulfate, 1.75 g of $CaCl_2$ dihydrate, 0.48 g of $MgCl_2$ hexahydrate, 12.5 g of sodium diphosphate decahydrate and 20 ml of isopropanol. The temperature of 30° C. was maintained for 30 minutes. Table 1 below shows the decoloring performance determined under these conditions, expressed in relation to the extinction value for the wash liquor containing red wine only (corresponding to 0% decoloring), the zero value (corresponding to 100% decoloring) being the extinction value of the pure wash liquor. It can be seen that the bleach activators used in accordance with the invention have superior decoloring performances to known activators.

TABLE 1

Bleaching Performance

| Activator | Decoloring [%] |
| --- | --- |
| B1 (32.5 mg) | 31 |
| C1 (18 mg) | 30 |
| C2 (53 mg) | 25 |
| C3 (31 mg) | 18 |

1 g of sodium perborate monohydrate and 0.3 g of the bleach activator to be tested were added to 100 ml of a solution containing 20 mg of morine per liter of deionized water, which was adjusted to pH 9.5 and kept at that pH throughout the following period of measurement by means of a pH stat, at a temperature of 20° C. which was also kept constant throughout the period of measurement. The extinction E of the solution at 400 nm was measured every minute for 30 minutes. Table 2 below shows the percentage decoloration values D(t) calculated in accordance with the equation $D(t)=[E(0)-E(t)/E(0)]*100$.

5-Benzoyloxy-2,4-pentadienoic acid (B2; see general formula II, R=phenyl) prepared from 5-benzoyloxy-2, 4pentadienal by Y. Cigata, M. Masaki and M. Ohta's method, as published in *Bull. Chem. Soc. Jpn.* 42 (1969), pages 224 et seq and, for comparison, N,N,N',N'-tetraacetyl ethylenediamine (C1; TAED), sodium-n-nonanoyloxybenzenesulfonate (C2; n-NOBS) were tested. The superiority of the bleach activator used in accordance with the invention is reflected in the results set out in Table 2 below.

TABLE 2

Percentage Decoloring as a Function of Time

| | Decoloring [%] after | | |
| --- | --- | --- | --- |
| Activator | 5 mins. | 15 mins. | 25 mins. |
| B2 | 21 | 70 | 76 |
| C1 | 4 | 52 | 70 |
| C2 | 4 | 49 | 63 |

What is claimed is:

1. A composition comprising:

(a) a peroxygen compound; and (b) an activator compound corresponding to formula I:

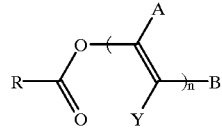

(I)

wherein R is hydrogen, an aryl, alkyl, alkenyl or cycloalkyl group containing 1 to 17 carbon atoms, n is a number from 1 to 8, A, B and Y, independently of one another, represent hydrogen, an aryl, alkyl, alkenyl or cycloalkyl group containing 1 to 17 carbon atoms or a hydrophilic group selected from the group consisting of $-SO_3H$, $-OSO_3H$, $-PO(OH)_2$, $-OPO(OH)_2$, $-CO_2H$ and anions thereof and $-N^+R^1R^2R^3\ X^-$, where $R^1$, $R^2$ and $R^3$, independently of one another, represent hydrogen, an aryl, alkyl, alkenyl or cycloalkyl group containing 1 to 17 carbon atoms and $X^-$ represents a charge-equalizing anion, and wherein at least one of the substituents A, B or Y in the molecule is one of the hydrophilic groups.

2. The composition of claim 1 wherein the activator compound is derived from an enol ester corresponding to formula II:

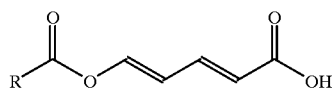

(II)

wherein R is hydrogen, an aryl, alkyl, alkenyl or cycloalkyl group containing 1 to 17 carbon atoms.

3. The composition of claim 1 wherein the activator compound is derived from an enol ester corresponding to formula III:

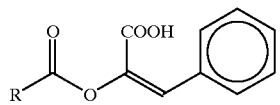

(III)

wherein R is hydrogen, an aryl, alkyl, alkenyl or cycloalkyl group containing 1 to 17 carbon atoms.

4. The composition of claims 1 wherein the peroxygen compound is selected from the group consisting of organic peracids, hydrogen peroxide, perborate, percarbonate and mixtures thereof.

5. The composition of claim 1 wherein R is selected from the group consisting of phenyl, $C_{1-11}$ alkyl, 9-decenyl and mixtures thereof.

6. A cleaning composition comprising:

(a) a peroxygen compound;

(b) an activator compound corresponding to formula I:

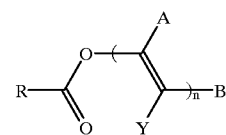

(I)

wherein R is hydrogen, an aryl, alkyl, alkenyl or cycloalkyl group containing 1 to 17 carbon atoms, n is a number from 1 to 8, A, B and Y, independently of one another, represent hydrogen, an aryl, alkyl, alkenyl or cycloalkyl group containing 1 to 17 carbon atoms or a hydrophilic group selected from the group consisting of $-SO_3H$, $-OSO_3H$, $-PO(OH)_2$, $-OPO(OH)_2$, $-CO_2H$ and anions thereof and $-N^+R^1R^2R^3\ X^-$, where $R^1$, $R^2$ and $R^3$, independently of one another, represent hydrogen, an aryl, alkyl, alkenyl or cycloalkyl group containing 1 to 17 carbon atoms and $X^-$ represents a charge-equalizing anion, and wherein at least one of the substituents A, B or Y in the molecule is one of the hydrophilic groups;

(c) a surfactant.

7. The composition of claim 6 wherein the activator compound is present in the composition in an amount of from 0.2 to 30% by weight, based on the weight of the composition.

8. The composition of claim 6 wherein the peroxygen compound is present in the composition in an amount of from 0.5 to 50% by weight, based on the weight of the composition.

9. The composition of claim 6 further comprising a component selected from the group consisting of an antimicrobial agent, a detergent builder, an enzyme, a solvent, a pH regulator, a dye transfer inhibitor, a soil redeposition inhibitor, an optical brightener, a foam inhibitor, a corrosion inhibitor and mixtures thereof.

10. The composition of claim 6 wherein the activator compound and peroxygen compound are present in the composition in a ratio of from 0.03 to 1 mole of activator compound per mole of peroxygen compound.

11. The composition of claim 6 wherein in formula I R is selected from the group consisting of phenyl, $C_{1-11}$ alkyl, 9-decenyl and mixtures thereof.

12. A process for activating a peroxygen compound in solution comprising reacting the peroxygen compound with an activator compound corresponding to formula I:

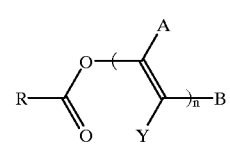

(I)

wherein R is hydrogen, an aryl, alkyl, alkenyl or cycloalkyl group containing 1 to 17 carbon atoms, n is a number from 1 to 8, A, B and Y, independently of one another, represent hydrogen, an aryl, alkyl, alkenyl or cycloalkyl group containing 1 to 17 carbon atoms or a hydrophilic group selected from the group consisting of $-SO_3H$, $-OSO_3H$, $-PO(OH)_2$, $-OPO(OH)_2$, $-CO_2H$ and anions thereof and $-N^+R^1R^2R^3\ X^-$, where $R^1$, $R^2$ and $R^3$, independently of one another, represent hydrogen, an aryl, alkyl, alkenyl or cycloalkyl group containing 1 to 17 carbon atoms and $X^-$ represents a charge-equalizing anion, and wherein at least one of the substituents A, B or Y in the molecule is one of the hydrophilic groups.

13. The process of claim 12 wherein the activator compound is derived from an enol ester corresponding to formula II:

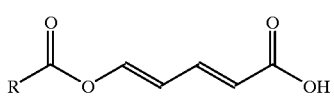

(II)

wherein R is hydrogen, an aryl, alkyl, alkenyl or cycloalkyl group containing 1 to 17 carbon atoms.

14. The process of claim 12 wherein the activator compound is derived from an enol ester corresponding to formula III:

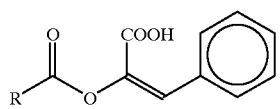

(III)

wherein R is hydrogen, an aryl, alkyl, alkenyl or cycloalkyl group containing 1 to 17 carbon atoms.

15. The process of claim 12 wherein the peroxygen compound is selected from the group consisting of organic peracids, hydrogen peroxide, perborate, percarbonate and mixtures thereof.

16. The process of claim 12 wherein R is selected from the group consisting of phenyl, $C_{1-11}$ alkyl, 9-decenyl and mixtures thereof.

17. The process of claim 12 wherein the activator compound and peroxygen compound are reacted at a ratio of from 0.3 to 1 mole of activator compound, per mole of peroxygen compound.

18. The process of claim 12 wherein the peroxygen compound is activated at a temperature below 60° C.

19. The process of claim 12 wherein the solution contains from 10 ppm to 10% of available oxygen.

20. The process of claim 12 wherein the solution contains from 50 to 5000 ppm of available oxygen.

* * * * *